United States Patent
Aurbach et al.

(10) Patent No.: US 6,713,212 B2
(45) Date of Patent: *Mar. 30, 2004

(54) HIGH-ENERGY, RECHARGEABLE ELECTROCHEMICAL CELLS

(75) Inventors: Doron Aurbach, Bnei Brak (IL); Orit Chasid, Zur-ig'al (IL); Yossi Gofer, Hod Hasharon (IL); Chaiim Gizbar, Holon (IL)

(73) Assignee: Bar-Ilan University, Ramat Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,707

(22) Filed: Jun. 1, 2001

(65) Prior Publication Data

US 2001/0049060 A1 Dec. 6, 2001

Related U.S. Application Data

(63) Continuation-in-part of application No. 09/419,940, filed on Oct. 18, 1999, now Pat. No. 6,316,141.

(51) Int. Cl.[7] .................................................. H01M 6/04
(52) U.S. Cl. ........................ 429/188; 429/199; 429/324; 429/319; 252/62.2
(58) Field of Search .............................. 429/303, 300, 429/304, 306, 319, 188, 199, 324, 220, 231.5, 231.6; 252/62.2

(56) References Cited

U.S. PATENT DOCUMENTS

| | | | |
|---|---|---|---|
| 4,104,450 A | | 8/1978 | Whitney et al. |
| 4,139,681 A | * | 2/1979 | Klemann et al. ............ 429/191 |
| 4,511,642 A | | 4/1985 | Higashi et al. |
| 4,894,302 A | | 1/1990 | Hoffman et al. |
| 4,917,871 A | * | 4/1990 | Dahn et al. ................... 423/61 |
| 5,491,039 A | | 2/1996 | Shackle |
| 5,849,432 A | | 12/1998 | Angell et al. |

FOREIGN PATENT DOCUMENTS

| | | |
|---|---|---|
| JP | 5-343065 | 12/1993 |
| JP | 6-223818 | 8/1994 |

OTHER PUBLICATIONS

Liebenow "*A Novel Type Of Magnesium Ion Conducting Polymer Electrolyte*" (Electrochimica Acta, Vol 43, Nos. 10–11, pp. 1253–1256. 1998) No month available.

* cited by examiner

*Primary Examiner*—Stephen Kalafut
*Assistant Examiner*—R Alejandro
(74) *Attorney, Agent, or Firm*—G. E. Ehrlich (1995) Ltd.

(57) ABSTRACT

A solid, gel type non-aqueous electrolyte for use in an electrochemical cell, the electrolyte including: (a) at least one polymer compound; (b) at least one organic solvent, and (c) at least one electrolytically active salt represented by the formula:

$$M'(ZR_nX_{q-n})_m$$

in which: M' is selected from the group consisting of magnesium, calcium, and aluminum; Z is selected from the group consisting of aluminum, boron, phosphorus, antimony and arsenic; R represents radicals selected from the following groups: alkyl, alkenyl, aryl, phenyl, benzyl, and amido; X is a halogen (I, Br, Cl, F); m=2–3; n=0–5 and q=6 for Z=phosphorus, antimony, and arsenic, and n=0–3 and q=4 for Z=aluminum and boron, wherein the polymer compound, organic solvent, and electrolytically active salt interact to form a non-aqueous electrolyte having a solid, gel type structure. The solid, gel type non-aqueous electrolyte is preferably incorporated into an electrochemical cell further including a metal anode and an intercalation cathode.

18 Claims, 2 Drawing Sheets

HIGH-ENERGY, RECHARGEABLE ELECTROCHEMICAL CELLS

This is a continuation-in-part of U.S. patent application Ser. No. 09/419,940 filed Oct. 18, 1999 now U.S. Pat. No. 6,316,141.

FIELD AND BACKGROUND OF THE INVENTION

The present invention relates to electrochemical cells utilizing a non-aqueous gel polymer electrolyte with an intercalation cathode, and more particularly, to electrochemical cells utilizing a non-aqueous gel polymer electrolytic system, an intercalation cathode and a magnesium anode.

Rechargeable, high energy density electrochemical cells of various kinds are known. Such cells usually consist of a transition metal oxide or chalcogenide cathode-active material, an anode-active alkali metal or alkali metal intercalation compound, and an electrolyte solution containing a dissolved alkali-based salt in an aprotic organic or inorganic solvent, or polymer electrolyte.

Theoretically, a rechargeable cell is capable of charging and discharging indefinitely, however, in practice such performance is unattainable. The degradation mechanisms of the various anodes, cathodes and electrolytes are complex and are known to those skilled in the art.

Two basic types of cathodes are appropriate for a battery system that is rechargeable at ambient temperatures. A liquid cathode can be used, allowing reactions to take place with facility. Liquid cathodes are also advantageous in that thin films or crusts forming on the surface of the cathode tend to crack, such that the cathode activity remains high over the course of the cycling. The mobility of the cathodic material is a liability, however, in that contact with the anode short-circuits the cell. Thus, an electrochemical cell with a liquid cathode requires protective, insulating films on the anode.

A solid cathode must be insoluble in the electrolyte, and must be able to absorb and desorb a charge-compensating ion in a substantially reversible and fast manner. A prime example of a solid cathode of this variety is an intercalation cathode. Intercalation chemistry focuses on the insertion of ions or neutral molecules into an inorganic or organic matrix. In a typical intercalation cathode, cations dissolved in the electrolyte solution are inserted into the inorganic matrix structure.

A group of intercalation materials of particular importance is called Chevrel-phase materials, also known as Chevrel compounds. Chevrel compounds contain an invariant portion consisting of molybdenum and a chalcogen—sulfur, selenium, tellurium, or mixtures thereof. The invariant portion is generally of the formula $Mo_6T_n$, where T represents the chalcogen and n is usually about 8. The unique crystal structure of Chevrel-phase materials allows the insertion of one or more metal ions in a reversible, partially reversible, or irreversible manner. The stoichiometry of the intercalation compound can be represented as $M_xMo_6T_n$, where M represents the intercalated metal and x may vary from 0 (no intercalated metal) to 4 or less, depending on the properties of the particular metal.

The intercalation of metal ions into the Chevrel compound releases energy. Since the process is partially or fully reversible, these compounds are particularly suitable as electrodes in electrochemical cells. For example, lithium, the predominant intercalation ion, can be removed from the Chevrel compound by the application of electrical energy. The energy is released as electrical energy upon reintercalation.

The cathode-active material in the high energy density, rechargeable electrochemical cells must be paired with a suitable anode-active material, which is most commonly made of an active metal such as alkali metals. However, the performance of a particular anode-cathode couple is strongly influenced by the nature of the electrolyte system. Certain non-aqueous electrolytes are known to perform well with a particular anode-cathode couple and be ineffective or significantly less effective with other anode-cathode couples, either because the electrolyte solution's components are not stable or because the solutions components degrades during cycling active electrodes. As a result, much of the prior art relates to the cathode-active material, the anode-active material and the electrolyte not only as independent entities, but also as units within an appropriate battery system.

U.S. Pat. No. 4,104,451 to Klemann et al., discloses reversible batteries with an alkali metal anode, a chalcogenide cathode, and organometallic alkali metal salts in organic solvents as the electrolyte system. Non-aqueous electrolyte systems containing alkali metal salts of boron or aluminum anions based which also contain organic groups are disclosed.

Organoborate salts of alkali metals represented by the formula

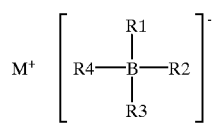

are disclosed in U.S. Pat. No. 4,511,642 to Higashi et al., wherein R1–R4 are organic radicals selected from the following groups: alkyl, aryl, alkenyl, cycloalkyl, allyl, heterocyclic, and cyano, and $M^+$ represents an alkali metal ion.

U.S. Pat. No. 4,139,681 describes cells containing electrolytically active metal salt complexes having the formula $ZMR_nX_i$, wherein Z is a metal from a group containing aluminum, the Rs are specified haloorganic radicals, the Xs are selected from various halides, alkyls, aryls, alkaryls and aralkyls. M is specified to be an alkali metal, with lithium being the preferred embodiment.

U.S. Pat. No. 4,542,081 to Armand et al., describes solutions for the constitution of solid electrolyte materials of electrochemical generators. The compound is of the formula

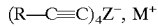

in which Z is a trivalent element capable of entering into 4-coordination, such as aluminum, and R represents groups which are non-proton donors. M is specified to be an alkali metal.

The prior art described above, including U.S. Pat. Nos. 4,104,451, 4,511,642, 4,139,681 and 4,542,081, specifies that M is an alkali metal. The use of an alkaline earth metal anode such as magnesium would appear disadvantageous relative to the use of an alkali metal such as lithium because alkali metal anodes are much more readily ionized than are alkaline earth metal anodes. In addition, on recharge the cell must be capable of re-depositing the anode metal that was dissolved during discharge, in a relatively pure state, and without the formation of deposits on the electrodes.

However, there are numerous disadvantages to alkali batteries. Alkali metals, and lithium in particular, are expensive. Alkali metals are highly reactive. Alkali metals are also highly flammable, and fire due to reaction of alkali metal with oxygen or other active material is extremely difficult to extinguish. Lithium is poisonous and compounds thereof are known for their severe physiological effects, even in minute quantities. As a result, the use of alkali metals requires specialized facilities, such as dry rooms, specialized equipment and specialized procedures.

In contradistinction, magnesium metal and aluminum metal are easy to process. The metals are reactive, but undergo rapid passivation of the surface, such that the metals exhibit highly stable behavior. Both magnesium and aluminum are inexpensive relative to the alkali metals.

U.S. Pat. No. 4,894,302 to Hoffman et al., discloses an electrochemical cell having an intercalation cathode, an alkaline earth anode, and a non-aqueous liquid electrolyte containing an organic solvent and an electrolytically active, organometallic alkaline earth metal salt represented by the formula

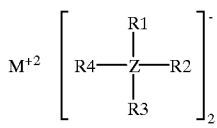

wherein Z is boron or aluminum; R1–R4 are radicals selected from the following groups: alkyl, aryl, alkaryl, aralkyl, alkenyl, cycloalkyl, allyl, heterocyclic alkyl, and cyano; and M represents an alkaline earth metal such as magnesium. The radicals can be inertly substituted with substituents that have no detrimental effect upon the electrolytic properties of the electrolyte composition with respect to effectiveness in an electrochemical cell, such as halogenated or partially halogenated derivatives of the above groups. While exhaustive care is taken to disclose a broad range of organic radicals and halogenated organic radicals, bonding the metallic species of the anion (Z) to another inorganic species is not considered.

U.S. Pat. No. 5,491,039 describes a solid, single-phase electrolyte containing a solid polymeric matrix and an organometallic ion salt represented by the formula $$M_c(ZR_n)$$

wherein Z is boron, aluminum or titanium; $R_n$ are various subsituted or unsubsituted organic radicals; M is lithium, sodium, potassium, or magnesium, c is 1 or 2, and n is an integer from 1 to 6. As in U.S. Pat. No. 4,894,302, a broad range of organic radicals including halogenated organic radicals is disclosed, but the bonding of the metallic species of the anion (Z) to another inorganic species is not reported. In all cases, metallic species Z is bonded to a carbon atom. More specifically, the bonding of the metallic species of the anion (Z) directly to a halogen is not disclosed. It must be emphasized that this is of particular significance in light of the fact that U.S. Pat. No. 5,491,039 teaches an extremely broad range of radicals that may be appropriate for attaching to the metallic species of the anion.

Both U.S. Pat. No. 5,491,039 and U.S. Pat. No. 4,894,302 disclose electrochemical cells having an alkaline earth anode such as magnesium. For commercial application, however, such magnesium batteries must be essentially rechargeable and must have a reasonable shelf life. Sustaining a voltage of 1.5 volts is problematic or impossible with the usual intercalation cathodes and electrolytes according to prior art. Magnesium batteries operating at 1.5 volts are particularly prone to electrolyte decomposition and to encrustation/passivation of both electrode surfaces.

In our co-pending parent application, Ser. No. 09/419,940, a new type of electrolyte for electrochemical cell was disclosed. The general formula of the electrolyte is $M'^{+m}(ZR_nX_{q-n})_m$ in which: M' is selected from the group consisting of magnesium, calcium, and aluminum; Z is selected from the group consisting of aluminum, boron, phosphorus, antimony and arsenic; R represents radicals selected from the following groups: alkyl, alkenyl, aryl, phenyl, benzyl, and amido; X is a halogen (I, Br, Cl, F); m=1–3; and n=0–5 and q=6 in the case of Z=phosphorus, antimony and arsenic, and n=0–3 and q=4 in the case of Z=aluminum and boron. The above-mentioned co-pending application disclosed the compatibility of this electrolyte type with Mg and a magnesium-Chevrel intercalation cathode of the form $$Cu_xMg_yMo_6S_8$$

to provide the basis for the production of a viable, rechargeable magnesium battery with a nominal voltage exceeding 1.5 volts.

Special interest is currently being focused on the use of solid polymeric electrolytes in advanced battery systems. The substitute of liquid electrolyte with solid gel polymeric electrolyte provides advantages in terms of safety, design flexibility and simplicity of production equipment and process operation.

Gels based on Li, Na and K ions are well known in academic literature and some of them have seen some extent of commercial implementation. By sharp contrast, very little work has been performed on gels based on Mg, Ca and Al ions. The relative paucity of work on Mg, Ca and Al gels may be attributed to several physical properties. The lattice energy of salts of Mg, Ca and Al is usually very high relative to those of salts of the alkali metals. Hence, it is extremely difficult to identify a polymer matrix that is polar enough to effectively cause ionic dissociation of these salts. It must be emphasized that the solubility of most of these salts is very low, even in water and in other high dielectric mediums, such that the possibility of finding a polymeric medium that can dissolve them with reasonable ionic dissociation appears remote. In addition, the ions of Mg, Ca, and Al are small and multivalent, such that the ions are characterized by extremely high charge densities, which tend to severely restrict ion mobility in solution. The transference number of such ions is expected to be less than 0.5 and the electrical conductivity of the solutions of such ions appear to be insufficient for the inventive electrolyte systems.

It must be further emphasized that the liquid electrolyte taught by our above-referenced co-pending parent application is based on a delicate equilibrium state in the solution. The electrochemical reactivity of the electrolyte is strongly dependent on the solvent structure and polarity. For example, the most extensively tested ethereal solvent in the above-referenced liquid electrolyte systems is tetrahydrofuran (THF). The use of very similar ether such as 2Me-THF, which differs from THF only by the addition of a single methyl group, was investigated. This seemingly minor difference has only a small effect on the polarity of the solvent, but in the inventive electrolyte system, such a difference was enough to cause a segregation of the complex salt and a loss in electrochemical reactivity. This example manifestly demonstrates that which is known on purely theoretical grounds, namely, that the solvent medium critically influences the structure and reactivity of the electrolyte complex salt.

Therefore, it would be surprising to find a polymer matrix in which the inventive electrolyte system will be soluble and compatible in such way that the complex will not segregate or react with the polymer matrix and the electrochemical reactivity will maintain.

Prior to the liquid electrolyte system taught by our above-referenced co-pending parent application, the only known type of electrolyte system in which magnesium could be electrochemically deposited and dissolved reversibly was a Grignard reagent in an ethereal solution. For example, Liebenow (Electrochimica Acta, Vol 43, Nos. 10–11, pp. 1253–1256, 1998) prepared a gel polymer based on ethyl magnesium bromide in tetrahydrofuran solution with polyethylene oxide as the polymeric matrix and demonstrated the ability of the system to reduce and oxidize magnesium. However, while gel polymers based on Grignard reagents may be of scientific interest, they cannot be applied to commercial battery technologies. The extremely poor anodic stability of gel polymers based on Grignard reagents precludes their use in such solid gel electrolytes. Moreover, the Grignard reagents are extremely flammable, corrosive and dangerous reduction materials.

Thus, there is a widely recognized need for, and it would be highly advantageous to have, a solid polymeric non-aqueous electrolyte that allows the production of an all solid, practical, rechargeable battery which would be more safe, clean, efficient and economical than rechargeable batteries known heretofore. It would be of further advantage if such an electrolyte would be based on magnesium, calcium, or aluminum, which are inexpensive and abundant raw materials.

SUMMARY OF THE INVENTION

The present invention is a new type of solid gel electrolyte for use in electrochemical cells. The properties of the solid gel electrolyte include high conductivity and an electrochemical window that can exceed 2.2V vs. $Mg/Mg^{+2}$. The use of the electrolyte in an appropriate cell promotes the substantially reversible deposition of the metal and a reversible intercalation process at the cathode material.

According to the teachings of the present invention there is provided a solid, gel type non-aqueous electrolyte for use in an electrochemical cell, the electrolyte including: (a) at least one polymer compound; (b) at least one organic solvent, and (c) at least one electrolytically active salt represented by the formula:

$$M'(ZR_nX_{q-n})_m$$

in which: M' is selected from the group consisting of magnesium, calcium, and aluminum; Z is selected from the group consisting of aluminum, boron, phosphorus, antimony and arsenic; R represents radicals selected from the following groups: alkyl, alkenyl, aryl, phenyl, benzyl, and amido; X is a halogen (I, Br, Cl, F); m=2–3; n=0–5 and q=6 for Z=phosphorus, antimony, and arsenic, and n=0–3 and q=4 for Z=aluminum and boron, wherein the polymer compound, organic solvent, and electrolytically active salt interact to form a non-aqueous electrolyte having a solid, gel type structure.

According to another aspect of the present invention, the solid, gel type non-aqueous electrolyte is incorporated into an electrochemical cell further including a metal anode and an intercalation cathode.

According to yet another aspect of the present invention, there is provided a non-aqueous electrolyte for use in an electrochemical cell, the electrolyte including: (a) at least one organic solvent, and (b) at least one electrolytically active salt represented by the formula:

$$M'(ZR_nX_{q-n})_m$$

in which: M' is selected from the group consisting of magnesium, calcium, and aluminum; Z is selected from the group consisting of aluminum, boron, phosphorus, antimony and arsenic; R represents radicals selected from the following groups: alkyl, alkenyl, aryl, phenyl, benzyl, and amido; X is a halogen (I, Br, Cl, F); m=2–3; n=0–5 and q=6 for Z=phosphorus, antimony, and arsenic, and n=0–3 and q=4 for Z=aluminum and boron.

According to yet another aspect of the present invention, the non-aqueous electrolyte is incorporated into an electrochemical cell further including a metal anode and an intercalation cathode.

According to further features in preferred embodiments of the invention described below, Z is aluminum.

According to further features in preferred embodiments of the invention described below, M' is magnesium.

According to further features in preferred embodiments of the invention described below, M' is calcium.

According to further features in preferred embodiments of the invention described below, the electrolytically active salt is $Mg[butylAlCl_3]_2$.

According to further features in preferred embodiments of the invention described below, the electrolytically active salt is $Mg[butylethylAlCl_2]_2$.

According to further features in preferred embodiments of the invention described below, M' is selected from the group consisting of magnesium and calcium, Z is aluminum, R represents at least one type of alkyl radical, and m is 2.

According to further features in preferred embodiments of the invention described below, the organic solvent contains tetraglyme.

According to further features in preferred embodiments of the invention described below, the organic solvent contains tetrahydrofuran.

According to further features in preferred embodiments of the invention described below, the polymer compound serves as a matrix.

According to further features in preferred embodiments of the invention described below, the polymer compound is selected from the group consisting of PVdF, PEO, and PVC.

According to further features in preferred embodiments of the invention described below, M' is selected from the group consisting of magnesium and calcium, Z is aluminum, R is at least one type of alkyl radical, and m is 2.

According to further features in preferred embodiments of the invention described below, the intercalation cathode is a Chevrel-phase intercalation cathode.

According to further features in preferred embodiments of the invention described below, the Chevrel-phase intercalation cathode is represented by the formula $$Cu_xMg_yMo_6S_8$$

wherein $1 \geq x > 0$ and $2 \geq y > 0$.

According to further features in preferred embodiments of the invention described below, the metal anode is magnesium.

According to further features in preferred embodiments of the invention described below, the polymer compound is selected from the group consisting of PVdF, PEO and PVC.

According to further features in preferred embodiments of the invention described below, the solvent is selected from the group consisting of THF and tetraglyme.

The present invention successfully addresses the shortcomings of the presently known solid gel electrolytes and provides the basis for the production of a viable, rechargeable battery based on magnesium, calcium, and aluminum, and having a nominal voltage exceeding 1.5 volts.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
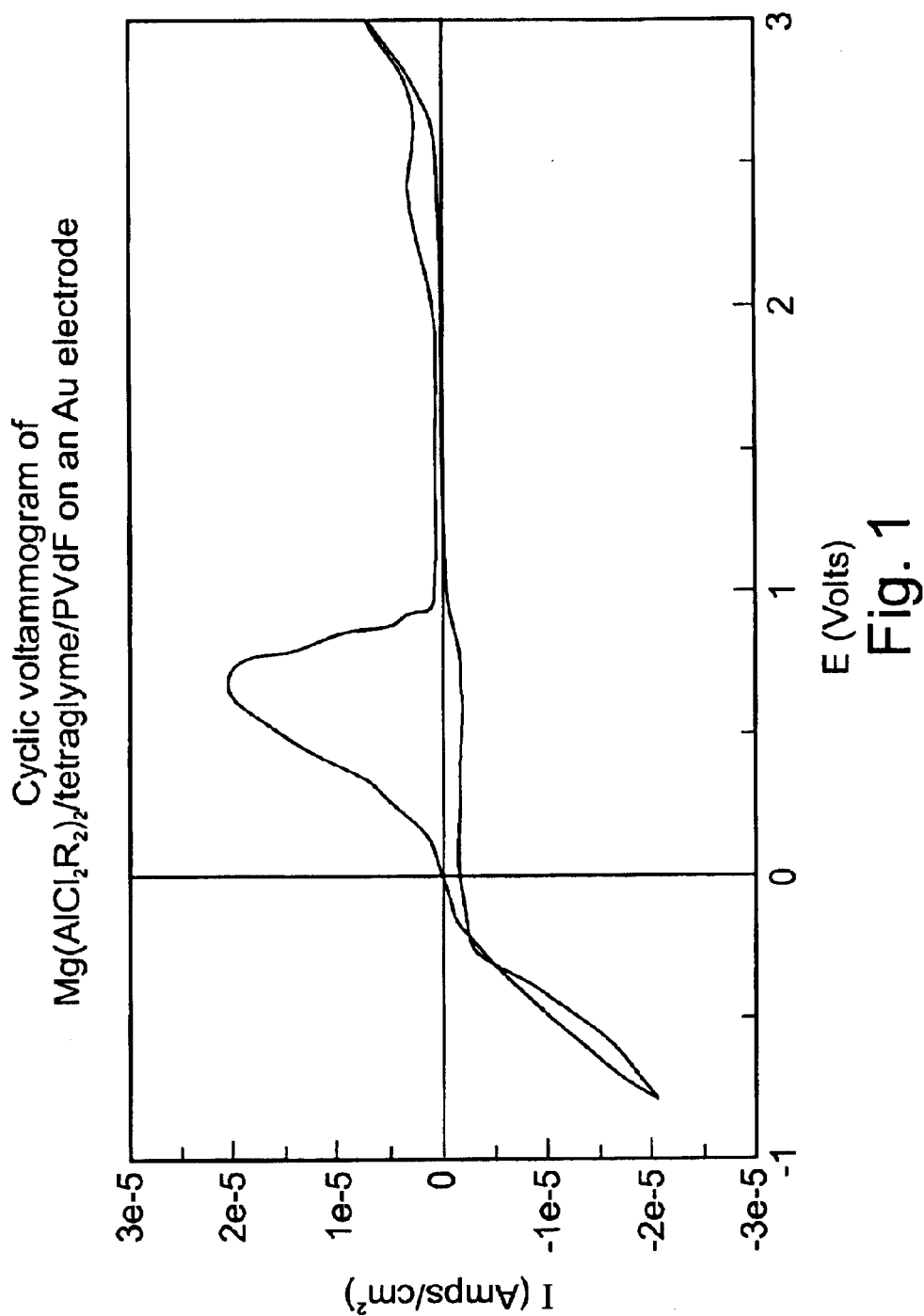
FIG. 1 is a graph displaying typical cyclic voltammogram of solid gel electrolyte containing a matrix of Mg(AlCl$_2$BuEt)$_2$ salt and tetraglyme in poly(vinylidene fluoride) (PVdF) using a gold electrode, according to the present invention.

The present invention is a new type of solid gel electrolyte for use in electrochemical cells. The properties of the solid gel electrolyte include high conductivity and an electrochemical window that can exceed 2.2V vs. Mg/Mg$^{+2}$. The use of the solid gel electrolyte in an appropriate cell promotes the substantially reversible deposition of magnesium metal on the anode current collector and the reversible intercalation of magnesium in the cathode material.

Although alkali metals are readily ionized, the use of other metal anodes, such as magnesium or aluminum has decided advantages. Magnesium and aluminum are very inexpensive relative to alkali metals. Alkali metals are highly reactive and highly flammable, and alkali fire is extremely difficult to extinguish. Lithium in particular is poisonous, and lithium compounds are known for their severe physiological effects, even in minute quantities. As a result, the use of alkali metals requires specialized facilities, such as dry rooms, specialized equipment and specialized procedures.

Magnesium and aluminum are reactive, but undergo rapid passivation of the surface, such that for all practical purposes, the metals are highly stable. Magnesium and aluminum are available and inexpensive, non-toxic, non-hazardous, and easy to work with, and as such, are highly desirable raw materials for electrochemical cells and for electrolytic solutions and solid gel electrolytes in particular.

Although primary electrochemical cells based on magnesium are known, such cells are non-rechargeable and are used solely for military applications. Sustaining a voltage of 1.5 volts is problematic or impossible with the usual intercalation cathodes and electrolytes according to prior art. Magnesium batteries operating at 1.5 volts are particularly prone to electrolyte decomposition and to encrustation/passivation of the electrode surface.

We have discovered that despite the known difficulties delineated above, a polymeric matrix in conjunction with a polar organic solvent, can dissolve the inventive electrolyte of the form:

This mixture creates a polymeric gel that exhibits sufficient conductivity at room temperature and that electrochemically deposits and dissolves the cation M' with high reversibility, despite all the limitations discussed above. The cation M' is selected from the group consisting of magnesium, calcium, and aluminum. More preferably, the cation M' is magnesium.

Z is selected from the group consisting of aluminum, boron, phosphorus, antimony and arsenic; R represents at least one type of radical selected from the following groups: alkyl, alkenyl, aryl, phenyl, benzyl, and amido; X is a halogen (I, Br, Cl, F); m=2–3; and n=0–5 and q=6 in the case of Z=phosphorus, antimony and arsenic, and n=0–3 and q=4 in the case of Z=aluminum and boron.

As used herein in the specification and in the claims section that follows, the radical "R" refers to at least one type of radical selected from the following groups: alkyl, alkenyl, aryl, phenyl, benzyl, and amido. Examples of electrolytically active salts having different R groups are Mg[butylethylAlCl$_2$]$_2$, Mg[benzylethylmethylAlCl]$_2$, and Ca[butylphenylAlCl$_2$]$_2$.

As used herein in the specification and in the claims section that follows, "PEO" refers to polyethylene oxide; "PVdF" refers to poly(vinylidene fluoride); "PVC" refers to poly(vinylchloride); "Bu" refers to a butyl group; "Et" refers to an ethyl group, and "THF" refers to tetrahydrofuran.

As described above, the electrochemical window of a cell with a solid gel electrolyte according to the present invention and an appropriate anode-cathode pair is 2.2 volts, such that the cell can be operated in a stable, reversible fashion at 1.5 volts without decomposition of the solid gel electrolyte and encrustation of the electrodes.

In a preferred embodiment of the invention, the solid gel electrolyte according to the invention functions in an electrochemical cell with a metal anode and an intercalation cathode.

Certain non-aqueous electrolytes are known to perform well with a particular anode-cathode couple and be ineffective or significantly less effective with other anode-cathode couples, either because the electrolyte is not inert or because it degrades during cycling. It is relevant, therefore, to treat the electrolyte, not only as an independent entity, but also as a unit within a system containing an appropriate anode-cathode pair.

Hence, according to further features in preferred embodiments of the invention described below, the solid gel electrolyte according to the present invention is incorporated into specific electrochemical cells containing an appropriate anode-cathode pair.

While various metals are suitable as anodes for the solid gel electrolytic system, including magnesium, lithium, aluminum and calcium, a particularly appropriate battery includes the solid gel electrolyte according to the present invention, a magnesium metal anode and a magnesium insertion compound cathode.

In yet another preferred embodiment, the magnesium insertion-compound cathode is a magnesium-Chevrel intercalation cathode of the form

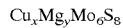

wherein x=0–1 and y=0–2.

The principles and operation of an electrolytic cell with an improved electrolyte according to the present invention may be better understood with the description provided hereinbelow and with reference to the drawings and the accompanying description provided in the Examples.

The solid electrolyte composition of the present invention includes a polymer compound, an organic solvent and electrochemically-active organometallic salts of the form M'(ZR$_n$X$_{q-n}$)$_m$, as described above. Organometallic salts of this form may be combined with compatible non-organometallic salts or with compatible organometallic salts of other forms.

Many types of polymer compounds can be use as matrix compound to form the solid gel electrolyte of the present invention, including poly(ethylene oxide) (PEO), poly (propylene oxide) (PPO), poly(vinylidene fluoride) (PVdF), poly(hexafluoropropylene) (HFP), poly(vinylchloride)

(PVC), poly(methyl metacrylate) (PMMA), poly (acrylonitrile) (PAN), (PEEK), (MEEP) and mixtures thereof.

Intercalation cathodes used in conjunction with the solid gel electrolyte according to the present invention include transition metal oxides, chalcogenides and halogenides and combinations thereof. More specifically, the transition metal oxides include $V_2O_5$, $TiS_2$, $MoS_2$, $ZrS_2$, $Co_3O_4$, $MnO_2$, $Mn_2O_4$, and the chalcogenides include Chevrel-phase compounds.

EXAMPLE 1

A magnesium-Chevrel intercalation cathode for use in conjunction with the solid gel electrolyte according to the present invention was synthesized according to the procedure developed by Goecke and Schölhorn, (E. Goecke, R. Schölhorn, G. Aselmann and W. Muller-Warmuth) published in *Inorg. Chem.* 26, 1805 (1987). Elemental sulfur, molybdenum and copper of high purity were added in a stoichiometric ratio of 4:3:1. After intimate mixing and pressing into pellets, the mixture was sealed in a quartz ampoule under a vacuum of $10^{-5}$ Torr. The ampoule was placed in a furnace, and the temperature was raised at a rate of 400° C./h to 450° C. The temperature was maintained at 450° C. for 24 hours. Again, the temperature was raised at a rate of 400° C./h to 700° C. and was maintained at 700° C. for 24 hours. The temperature was then raised at a rate of 120° C./h to 1050° C. and was maintained at 1050° C. for 48 hours. After cooling to room temperature at a rate of 120° C./h, the ampoule was broken open. The copper molybdenum sulfide ($Cu_2Mo_6S_8$) obtained was milled into fine powder using mortar and pestle.

The copper molybdenum sulfide powder was mixed with Teflon-loaded carbon black (CB). The resulting paste was spread on stainless steel mesh and pressed. The composite electrode formed was dried under vacuum at room temperature for 24 hours.

The electrode was subsequently subjected to either chemical or electrochemical pretreatment in which some of the copper ions in the host matrix ($Cu_2Mo_6S_8$) were deinserted. The electrochemical deintercalation of copper was performed in a non-aqueous medium, a 1M solution of $Mg(ClO_4)_2$ in acetonitrile. The deinsertion was performed by a galvanostatic charging process in which the upper limit of the potential was controlled. A chemical deintercalation of the copper was carried out by a direct reaction of $Cu_2Mo_6S_8$ with aqueous acidic solution containing $FeCl_3$ as an oxidizer.

After thorough washing in acetonitrile and subsequent drying of the electrode, charging-discharging cycles were conducted in a 1M solution of $Mg(ClO_4)_2$ in acetonitrile at various scan rates between −1.6 V and 0.01 V, relative to the $Ag/Ag^{+1}$ reference electrode. A pronounced electrochemical redox activity was observed, with a main oxidation peak at −1.219 V vs. $Ag/Ag^+$ and a corresponding main reduction peak at −1.41 V vs. $Ag/Ag^+$. The charge associated with the intercalation-deintercalation process was 71 mAh/g and 72 mAh/g, respectively, which correspond to y=1.09–1.12 in the formula

$$Cu_{0.13}Mg_yMo_6S_8$$

The chemical and electrochemical reversibility of the intercalation process was demonstrated over multiple cycles.

EXAMPLE 2

Referring now to the drawings, FIG. 1 is a graph displaying typical cyclic voltammogram of an electrochemical cell including using a gold electrode, a solid gel electrolyte containing a PVdF matrix with an ether-magnesium organohalo-aluminates salt and tetraglyme solvent.

FIG. 1 shows the potentiodynamic behavior of $Mg(AlCl_2BuEt)_2$ obtained with tetraglyme in a PVdF matrix using a gold working electrode. The peak at −0.8 V is due to the deposition of magnesium metal, and the peak at around 0.7 V is attributed to the subsequent electrochemical dissolution of the magnesium metal. The electrochemical window obtained with this system exceeds 2.2 V. It is clearly evident from the cyclic voltammogram that the process of magnesium deposition and dissolution is fully reversible.

EXAMPLE 3

An electrochemical cell was prepared consisting of a Chevrel-phase cathode, a magnesium metal anode, and a solid gel electrolyte containing PVdF, $Mg(AlCl_2BuEt)_2$ salt and tetraglyme. The cathode, weighing 74.3 mg, was made from a mixture of copper-leached Chevrel-phase material containing 10 weight-% carbon black and 10 weight-% PVdF as a binder, spread on stainless steel mesh. The solid gel electrolyte was prepared from 0.25 Molar $Mg(AlCl_2BuEt)_2$ salt and tetraglyme in a PVdF matrix. The anode was a disc of pure magnesium metal, with a diameter of 16 mm and a thickness of 0.2 mm. The battery was encased in a stainless steel "coin type" cell configuration without a separator. The cell was cycled on a standard charger-discharger with a current density of 23.3 milliamperes/gram. The potential limits for the cycling were between 0.5 V at the fully discharged state and 1.8 V for the fully charged state.

Figure 2:
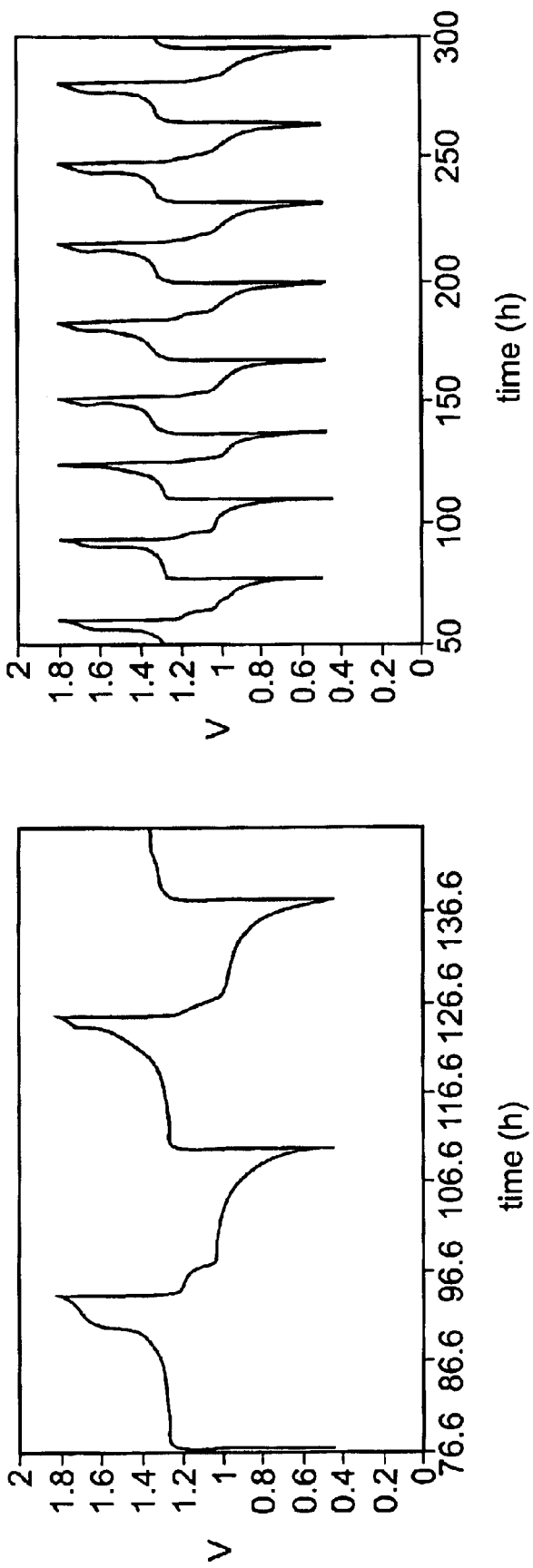
FIG. 2 is a graph of the voltage patterns of an electrochemical cell consisting of a Chevrel-phase cathode, magnesium metal anode, and a solid gel electrolyte containing a matrix of Mg(AlCl$_2$BuEt)$_2$ salt and tetraglyme in poly (vinylidene fluoride) (PVdF), according to the present invention.

The battery was subjected to continuous cycling over 3 months. The good cyclability of the battery is clearly evident from FIG. 2, in which several cycles are represented. The battery performance remains strong over the entire length of the experiment. The measured charge density obtained in each discharge is 61 mAh per gram of the cathode material.

EXAMPLE 4

A solid gel electrolyte according to the present invention was prepared as follows: commercial, reagent-grade $MgBu_2$, was dissolved in heptane. Commercial, reagent-grade $AlEtCl_2$ was added drop wise to the $MgBu_2$ solution according to the molar ratio. The mixture was stirred for 48 hours under an inert gas, and $Mg(BuEtAlCl_2)_2$ was crystallized out of solution. The solvent was removed by evacuation. Ether solvents were added very slowly to the organomagnesium salt to produce a saturated solution (around 0.5M). A commercially available PVdF powder for gel polymer application was added to the above solution and the mixture was stirred and heated until a one phase polymeric gel was formed.

It will be appreciated that the above descriptions are intended only to serve as examples, and that many other embodiments are possible within the spirit and the scope of the present invention.

What is claimed is:
1. An electrochemical cell comprising:
  (a) a metal anode;
  (b) a cathode; and
  (c) a non-aqueous electrolyte including:
    (i) at least one organic solvent and

(ii) at least one electrolytically active salt represented by the formula:

in which:
M' a cation selected from the group consisting of magnesium, calcium, and aluminum;
Z is selected from the group consisting of aluminum, boron, phosphorus, antimony and arsenic;
R represents radicals selected from the following groups: alkyl, alkenyl, aryl, phenyl, benzyl, and amido;
X is a halogen (I, Br, Cl, F);
m=2–3;
n=0–5 and q 6 for Z phosphorus, antimony, and arsenic, and n=0–3 and q=4 for Z aluminum and boron;
wherein said metal anode and said cation include an identical metal selected from the group consisting of magnesium, calcium, and aluminum.

2. The electrochemical cell of claim 1, wherein said non-aqueous electrolyte further includes:

(iii) at least one polymer compound.

3. The electrochemical cell of claim 2, wherein said polymer compound, said organic solvent, and said electrolytically active salt interact to form a non-aqueous electrolyte having a solid, gel type structure.

4. The electrochemical cell of claim 1, wherein said identical metal is magnesium.

5. The electrochemical cell of claim 1, wherein said metal anode is magnesium.

6. The electrochemical cell of claim 1, wherein Z is aluminum.

7. The electrochemical cell of claim 1, wherein M' is calcium.

8. The electrochemical cell of claim 1, wherein said electrolytically active salt is $Mg[butylAlCl_3]_2$.

9. The electrochemical cell of claim 1, wherein said electrolytically active salt is $Mg[butylethylAlCl_2]_2$.

10. The electrochemical cell of claim 1, wherein M' is selected from the group consisting of magnesium and calcium, Z is aluminum, R represents at least one type of alkyl radical, and m is 2.

11. The electrochemical cell of claim 2, wherein said organic solvent contains tetraglyme.

12. The electrochemical cell of claim 1, wherein said cathode is an intercalation cathode.

13. The electrochemical cell of claim 12, wherein said intercalation cathode is a Chevrel-phase intercalation cathode.

14. The electrochemical cell of claim 13, wherein said Chevrel-phase intercalation cathode is represented by the formula

wherein $1 \geq x > 0$ and $2 \geq y > 0$.

15. The electrochemical cell of claim 2, wherein said polymer compound includes poly(vinylidene fluoride).

16. The electrochemical cell of claim 2, wherein said polymer compound includes polyethylene oxide (PEG).

17. The electrochemical cell of claim 2, wherein said polymer compound includes poly(vinylchloride) (PVC).

18. The electrochemical cell of claim 2, wherein said solvent contains tetrahydrofuran (THF).

* * * * *